United States Patent
Sayet

(10) Patent No.: US 9,770,597 B2
(45) Date of Patent: Sep. 26, 2017

(54) TELEMETRY PORT FOR IMPLANTED MEDICAL DEVICE

(71) Applicant: Precision Medical Devices, Inc., Fort Lauderdale, FL (US)

(72) Inventor: Peter Sayet, Fort Lauderdale, FL (US)

(73) Assignee: Precision Medical Devices, Inc., Fort Lauderdale, FL (US)

( * ) Notice: Subject to any disclaimer, the term of this patent is extended or adjusted under 35 U.S.C. 154(b) by 0 days.

(21) Appl. No.: 14/837,135

(22) Filed: Aug. 27, 2015

(65) Prior Publication Data

US 2017/0056673 A1  Mar. 2, 2017

(51) Int. Cl.
*A61N 1/375* (2006.01)
*A61N 1/372* (2006.01)

(52) U.S. Cl.
CPC .......... *A61N 1/375* (2013.01); *A61N 1/3758* (2013.01); *A61N 1/37211* (2013.01)

(58) Field of Classification Search
CPC  A61N 1/37211; A61N 1/37229; A61N 1/375; A61N 1/3758
USPC .................................................. 607/36, 60
See application file for complete search history.

(56) References Cited

U.S. PATENT DOCUMENTS

| | | | |
|---|---|---|---|
| 6,701,188 B2 | 3/2004 | Stroebel et al. | |
| 6,868,288 B2 | 3/2005 | Thompson | |
| 7,337,003 B2 | 2/2008 | Malinowski | |
| 7,447,533 B1 | 11/2008 | Fang et al. | |
| 8,060,212 B1 | 11/2011 | Rios et al. | |
| 8,160,705 B2 | 4/2012 | Stevenson et al. | |
| 8,527,060 B2 | 9/2013 | Amely-Velez et al. | |
| 8,843,206 B2 * | 9/2014 | Judkins ............... | A61N 1/37223 607/60 |
| 2004/0015039 A1 | 1/2004 | Melvin | |
| 2004/0176815 A1 | 9/2004 | Danzig et al. | |
| 2005/0149139 A1 * | 7/2005 | Plicchi .................... | A61N 1/375 607/32 |
| 2005/0182451 A1 | 8/2005 | Griffin et al. | |
| 2008/0288021 A1 | 11/2008 | Schmid | |
| 2009/0163979 A1 * | 6/2009 | Hjelm ................. | A61N 1/37229 607/60 |
| 2009/0228072 A1 | 9/2009 | Coe et al. | |
| 2010/0019985 A1 * | 1/2010 | Bashyam .............. | A61B 5/0031 343/873 |
| 2010/0082080 A1 | 4/2010 | Mateychuk | |
| 2010/0109966 A1 * | 5/2010 | Mateychuk ........ | A61N 1/37229 343/841 |
| 2012/0326886 A1 | 12/2012 | Herman et al. | |
| 2014/0025039 A1 | 1/2014 | Rajendra et al. | |
| 2015/0223905 A1 | 8/2015 | Karmarkar et al. | |

* cited by examiner

*Primary Examiner* — Allen Porter, Jr.
(74) *Attorney, Agent, or Firm* — Jacqueline Tadros; Jacqueline Tadros, P.A.

(57) ABSTRACT

A telemetry port for providing an open space in which an antenna may transmit and receive signals free from interference from the metal shell of an implantable medical device, the telemetry port includes a housing defining a void space for receiving an antenna. The void space is configured to provide the antenna with sufficient space such that the antenna does not contact the housing. The housing further includes a periphery positioned along a bottom edge capable of being integrated to an implantable medical device, and forming a hermetic seal with the implantable medical device.

15 Claims, 3 Drawing Sheets

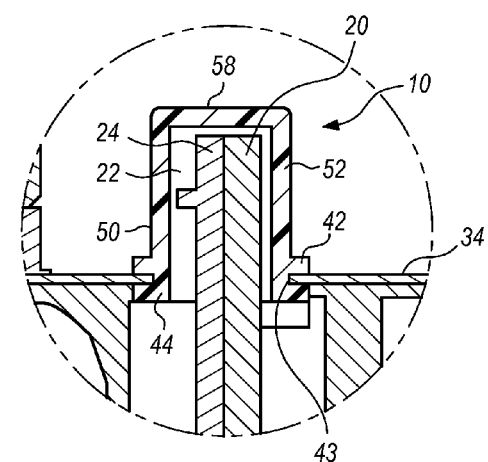
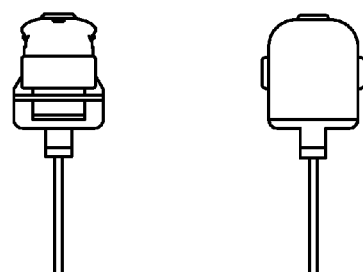
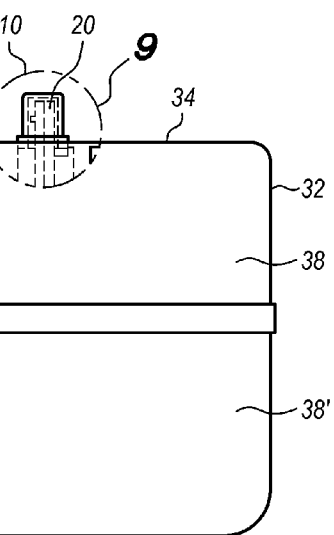
FIG. 7  FIG. 8

TELEMETRY PORT FOR IMPLANTED MEDICAL DEVICE

BACKGROUND OF THE INVENTION

1. Field of the Invention

The invention relates generally to electronic medical devices implanted within an animal or human body, and in particular the invention relates to fully implanted electronic medical devices including a telemetry communication mechanism.

2. Description of Related Art

Implantable electronic medical devices (IMD) often need to communicate with other devices, such as another IMD or an external device, such as for example, a monitoring system or programming console.

A telemetry communication system sends and receives information in a bidirectional mode. The system sends or receives commands to a separate device that might cause the separate device to alter its electronic or electro-mechanical performance, thereby controlling the device. The system may consist of hardware and software, sensors, a transmission protocol, and normally some form of a display, and possibly hardware and software capable of recording such interactions.

Telemetry systems can be implemented to acquire and transmit data from a remote implanted source to provide information about the implanted device and a user's activities.

It is desirable for physicians to exercise control over an IMD or to otherwise obtain information regarding the operational status of an IMD.

IMD's perform certain tasks to render treatment for various medical conditions. IMD's that are designed to include a remote control telemetry mechanism require that the device send and/or receive remote control telemetry commands. It is critical that the main electronic parts and power supply of the IMD are hermetically sealed within the shell of the IMD, in order to guard the subject's internal tissue from possible leakage of, or contact with, toxic components within the IMD and also prevent the incursion of internal bodily fluids into the shell of the IMD. The main electronic parts and power supply of IMD's are hermetically sealed in a hard-shell case, usually made of some form of metallic material, such as for example titanium. It is appreciated that the shell casing of the IMD may be formed of another suitable material.

Metallic compounds are effective materials for comprising the shell of an IMD because they are non porous, inert and highly durable. They are disadvantageous however because metals interfere or block remote telemetry signals going to and from the electronic receivers.

The medical device industry, as a whole, has been utilizing materials, such as titanium in the construction of shells for IMD's for their durability, inertness and air and fluid tightness for not only the protection of the various electronic parts that are being encased from a subject's bodily fluids, but also for the protection of the implant subject's tissue from being exposed to potentially toxic or otherwise harmful elements that may be associated with the implanted components within the IMD.

In such instances however, problems arise, since remote control commands are unable to be received or sent on a uniform basis to or from the electronic components encased within the metallic shell or case of the IMD.

Short and long term implant tests of prospective materials for IMD's have identified problems associated with using plastic especially when the implanted device includes an on-board power supply. The problems include, but are not limited to, porosity that may allow for the incursion of internal bodily fluids into the case, as well as, possible off-gassing issues that could alter the plastic shell's structural integrity.

The prior art includes various attempts to reduce or overcome interference in sending/receiving telemetry signals from implanted electronic medical devices. For example, U.S. Pat. No. 6,868,288 B2 (to Thomson) is a telemetry receiver for an implantable medical device (IMD) with an RF antenna coupled to a telemetry circuit that includes an out-of-band rejection filter comprising a thin film bulk acoustic resonator filter.

U.S. Pat. No. 8,160,705 B2 (to Stevenson et al.) provides for an EMI filter terminal assembly for an AIMD including a radio frequency (RF) telemetry pin antenna extending therethrough, including a conductive shield extending over a portion of the RF telemetry pin antenna in non-conductive relation with the telemetry pin, and conductively connected to a ground associated with the AIMD.

U.S. Pat. No. 8,527,060 B2 (to Amely-Velez et al.) teaches a shield that is configured to preserve telemetry communications between an AIMD in a patient and a telemetry wand when in an environment having high power electromagnetical interferers. The shield may include a plastic composition, include a shell including a wall that defines a volume and an opening in the shell. The volume may be configured to receive therein the telemetry wand such that the second and lateral sides of the telemetry wand face respective portions of the wall and the first side faces the opening in the shell.

U.S. Pat. Publ. No. 2012/0326886 A1 (to Herman et al.) discloses a telemetry head for communication with an implantable medical device comprises a telemetry antenna and a shield substantially surrounding at least a portion of the antenna, the shield having a coating comprising a ferromagnetic material applied to at least a portion of the shield, wherein the coating is configured to shield at least the portion of the telemetry antenna from electromagnetic interference fields while permitting telemetry signals to pass through the coating.

Thus, it is desirable to expose an antenna in an IMD to remotely broadcasted signals without subjecting the antenna to interference from the metallic shell of an IMD.

SUMMARY OF THE INVENTION

The present invention allows remote telemetry antennae to gain unfettered access to remotely broadcasted signals without interference by using a telemetry port in which to house the antennae. The telemetry port is formed of a non metallic, preferably plastic compound that is capable of securely bonding with the metallic shell of the IMD. The material for the telemetry port should be durable and capable of protecting human tissue and internal bodily fluids from contact with any of the mechanical, electronic or power supply components within the IMD, as well as allowing for unfettered bidirectional telemetry signals.

The present invention is described as an extension cover or a port, protruding out of a telemetry box or monitor, wherein the telemetry box may include a titanium or other metallic shell enclosure. It is noted herein that a telemetry box is one form of an IMD. A bottom portion of the telemetry port is hermetically sealed to the titanium or other metallic shell enclosure. In a preferred embodiment the telemetry port includes a flexible transparent plastic material. The telemetry port provides an interference free transmission zone for internal telemetry antennae that extend up from the telemetry box into the void space within the protruding telemetry port, beyond the metallic shell enclosure of the telemetry box or monitor. The internal telemetry antennae are thereby able to transmit and receive signals free from interference from the metallic or titanium shell of the telemetry box. It is to be appreciated that there may be one or more than one antenna within a telemetry port at any given time.

The antennae are positioned within the telemetry port but are not solidly encased within the telemetry port. Thus, the antenna or antennas within the telemetry port are completely unrestricted. The telemetry port provides the antennae with sufficient room to move around within the port without contacting the telemetry port, thereby avoiding a possible disruption of connection with a transmitter or receiver that may occur if the antenna contacted the housing/shell of the telemetry port, such as may occur if the antenna was solidly encased.

Accordingly, one aspect of the present invention is to provide a "free zone" wherein remote telemetry commands can be sent or received without interference from the titanium, or other metallic shell of the telemetry box.

Another aspect of the present invention is that it includes a material that is capable of binding with the metallic shell material of the telemetry box in such a way as to be able to continue to ensure that the bond is of a nature that the entire shell component of the IMD remains completely hermetically sealed without creating the possibility of bodily fluid incursion.

In a preferred embodiment, the telemetry port of the present invention is fabricated of a very durable flexible plastic material suitable for allowing the unimpeded transmission and reception of remote telemetry commands.

At least a portion of the material of the telemetry port must also be capable of tightly bonding with the material of the shell of the telemetry box, so as to form a hermetic seal with the telemetry box.

The telemetry port of the present invention can be made in a broad range of dimensions and/or shapes. The telemetry port can be made of a broad range of materials, as long as the material allows for the free flow of telemetry signals and is capable of hermetically bonding with the shell of the main body of the telemetry box or IMD.

In a preferred embodiment, a clear flexible plastic material is used to form the telemetry port. Plastic is used to prevent the signal from bouncing back off of a titanium shell of the main body of the telemetry box.

The telemetry port of the present invention provides a means of allowing the remote telemetry receiving antennae to gain unfettered access to the reception and transmission of signals. The main body of the telemetry box or IMD houses mechanical, electronic and power supply components.

An advantage of the present invention is that the protruding telemetry port is hermetically sealed to the main body of the IMD.

An objective of the present invention is for the telemetry port to provide a "free transmission" zone for the leads of the telemetry antennae in order to prevent signal interference and to improve signal transmission and reception.

Another advantage of the telemetry port of the present invention is that it is capable of both continuing to protect human tissue and internal bodily fluids from contact with any of the mechanical, electronic or power supply components inside the main body of the IMD and vice versa, as well as, allow for unfettered bidirectional telemetry signal transmission and reception.

Yet another advantage of the present invention is that it allows the antenna within the telemetry port to move freely without contacting the housing of the telemetry port.

The above mentioned and other features and advantages of this invention, and the manner of attaining them, will become more apparent and the invention itself will be better understood by reference to the following description of embodiments of the invention taken in conjunction with the accompanying drawings.

It is noted that references made herein to the present invention or aspects of the invention thereof should be understood to mean certain embodiments of the present invention and should not necessarily be construed as limiting all embodiments to a particular description. The present invention is set forth in various levels of detail in the Summary of the Invention as well as in the attached drawings and the Detailed Description of the Invention and no limitation as to the scope of the present invention is intended by either the inclusion or non-inclusion of elements, components, etc. in this Summary of the Invention. Additional aspects of the present invention will become more readily apparent from the Detail Description, particularly when taken together with the drawings.

BRIEF DESCRIPTION OF DRAWINGS

FIG. 7 is a side view of an alternative embodiment of the present invention.

FIG. 8 is a front view of an alternative embodiment of the present invention shown in FIG. 8.

FIG. 9 is a close-up view of the telemetry port of the present invention as shown in FIG. 8.

DETAILED DESCRIPTION OF THE DRAWINGS

Figure 1:
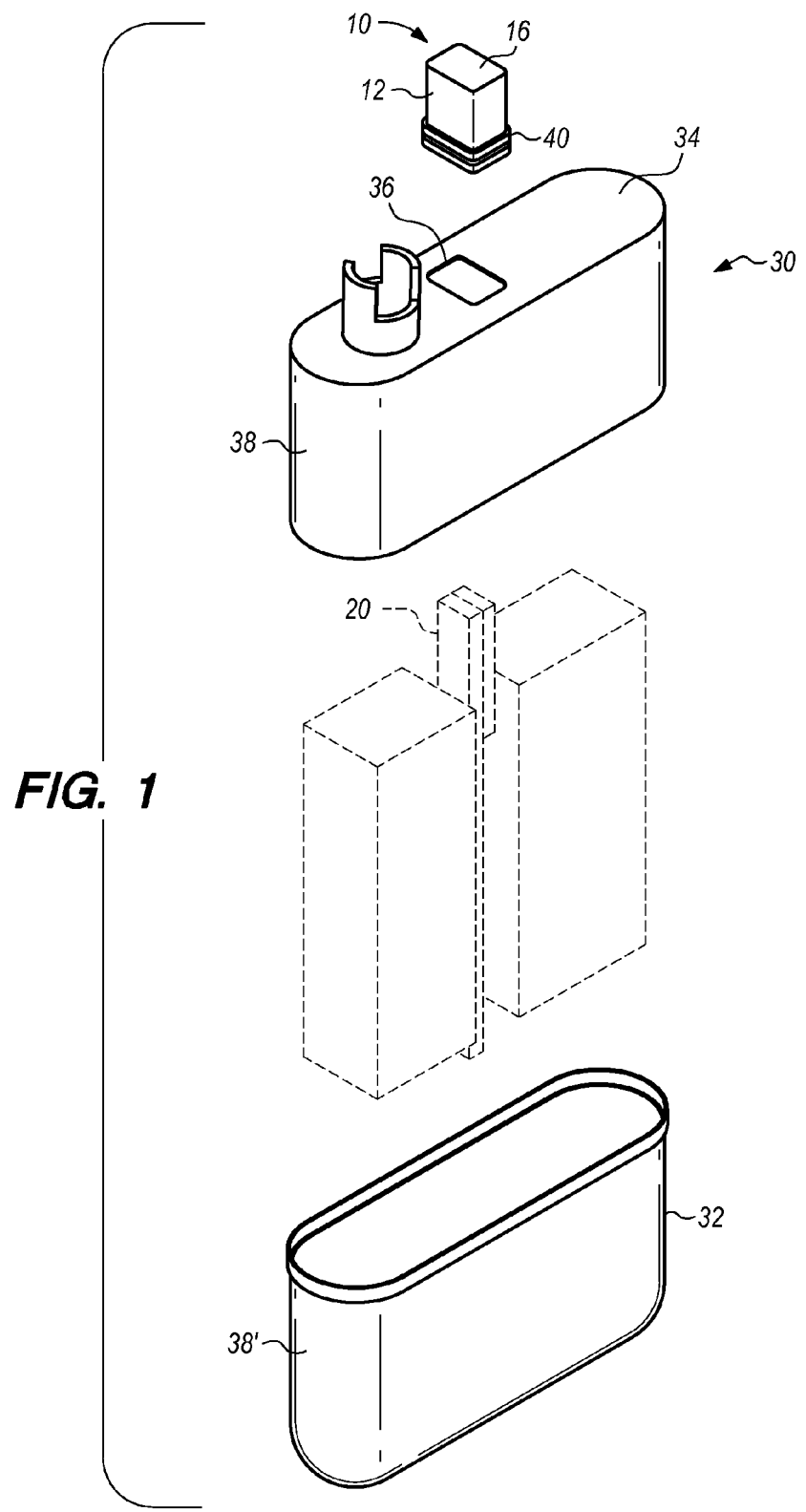
FIG. 1 is an exploded view of the telemetry port of the present invention in conjunction with an implantable electric device.

The detailed embodiments of the present invention are disclosed herein. It should be understood, however, that the disclosed embodiments are merely exemplary of the invention, which may be embodied in various forms. Therefore, the details disclosed herein are not to be interpreted as limited, but merely as the basis for the claims and as a basis for teaching on skilled in the art how to make and/or use the invention.

Referring now to FIGS. 1-9 the subject invention is a telemetry port 10 for providing an open space in which an antenna 20 may transmit and receive signals free from interference from a metal shell 32 of an IMD 30. It is appreciated that the shell 32 may include one or more segments. In one embodiments, the shell includes segments 38 and 38'. The telemetry port 10 comprises a material that is permeable to sending and receiving telemetry signals and allows free and clear ingress and egress of telemetry signals. In a preferred embodiment, the material of the telemetry port 10 is a clear flexible plastic. It is to be appreciated that the material of the telemetry port 10 may also comprise a hard plastic, a non-clear plastic, or another material, so long as the material is permeable to telemetry signals and at least a portion of the telemetry port 10 is capable of forming a hermetic seal with the metal shell 32.

The telemetry port 10 includes a housing 12 defining a void space 16 therein for receiving an antenna 20 within the void space 16. The void space 16 is of sufficient size to allow the antenna 20 therein to engage in the free flow of telemetry signals within the telemetry port 10.

The void space 16 is configured to provide the antenna 20 positioned therein with sufficient space such that the antenna 20 does not contact the housing 12 of the telemetry port 10. There is a gap 22 that is defined between the antenna 20 and the housing 12. The gap 22 is of sufficient size relative to the antenna 20, to allow for freedom of movement of the antenna 20 within the housing 12, such that the antenna 20 can move freely in any direction within the housing 12 as a result of vibrational movement without contacting the housing 12. Movement of the antenna 20 within the telemetry port 10 may result from vibrational movement or other mechanical movement, such as, for example, if the antenna 20 is retracted or otherwise retractable.

The housing 12 of the telemetry port 10 includes a periphery 40. The periphery 40 is positioned along a bottom edge of the housing 12 of the telemetry port 10. The periphery 40 is configured to integrally mate with the IMD 30. In a preferred embodiment, the periphery 40 mates with a rim 34 of the IMD 30 when the telemetry port 10 is in integral communication with the IMD 30. The periphery 40 further includes a durable material that is capable of forming a hermetic seal with the shell 32 of the IMD 30.

A hermetic seal between the telemetry port 10 and the IMD 30 is needed to prevent the incursion of bodily fluid into the IMD 30 or telemetry port 10 or leakage of, or contact with, potentially toxic material from components within the IMD 30 and the subject's internal tissue. A hermetic seal between the periphery 40 of the telemetry port 10 and the shell 32 of the IMD 30 at the rim 34 may be achieved using a laser or sonic, or another welding process. It is noted that the telemetry port 10 may be hermetically sealed to the shell 32 the IMD 30 using other methods as will be appreciated by one reasonably skilled in the art.

The periphery 40 of the telemetry port 10 includes a first band 42, a second band 44 and a ring 43, positioned intermediate to the first band 42 and second band 44, the ring 43 further having a circumference that is generally smaller than the circumference of each of the first band 42 and the second band 44 such that the ring 43 forms a groove and is indented relative to each of the first band 42 and second band 44.

In one embodiment, the housing 12 of the telemetry port 10 comprises a first side wall 50 a second side wall 52 the second side wall 52 being generally opposite to the first side wall 50, a first lateral side 54 and a second lateral side 56, the second lateral side 56 being generally opposite to the first lateral side 54 and contiguous to the first side wall 50 and second side wall 52, a top face 58 positioned along a topmost edge of each of the first side wall 50, second side wall 52, first lateral side 54 and second lateral side 56, the top face 58 positioned intermediate to the first side wall 50 and second side wall 52 and further extending therebetween, from the first side wall 50 to the second side wall 52, and from the first lateral side 54 to the second lateral side 56.

The first band 42 of the periphery 40 is configured to mate with the IMD 30, at an aperture 36 above the rim 34 and the second band 44 is configured to mate with the IMD 30 below the rim 34, when the periphery 40 of the telemetry port 10 is in integral communication with the IMD 30 such that the periphery 40 and the rim 34 of the IMD 30 are in sealing engagement. When the periphery 40 of the telemetry port 10 and the rim 34 of the IMD 30 are in sealing engagement, the ring 43 is generally level with the rim 34 of the IMD 30.

The aperture 36 provides a point of ingress and egress to the antenna 20 from within the shell 32 of the IMD 30 and the telemetry port 10.

In a preferred embodiment, the void space 16 of the telemetry port 10 is of a sufficient size to allow for ingress or egress of the antenna 20. It is noted that the antenna 20 may be retractable.

In another embodiment, the void space 16 of the telemetry port 10 is of sufficient size to allow for ingress or egress of an antenna 20 with an on board or integrated PC board 24.

In yet another embodiment, a portion of the antenna 20 sufficient to freely receive and transmit signals is projected within the void space 16 of the telemetry port 10.

In another embodiment of the invention, the telemetry port 10 is affixed to the shell 32 of the IMD 30.

The telemetry port 10 allows portions of the antenna 20 that are within the telemetry port 10 to move freely within the telemetry port 10 without contacting the housing 12 of the telemetry port 10 to allow space for movement of the antenna 20 within the telemetry port 10 that may arise under various circumstances. For example, movement of the antenna 20 may arise as a result of vibration or when the antenna 20 are being moved in and out of the telemetry port 10.

The telemetry antenna 20 allow for signal transmission and reception and may include an on board PC-board 24. It is appreciated that the antenna 20 may comprise various sizes, shapes and configurations. In a preferred embodiment, the antenna 20 comprises a solid projection affixed to an on-board PC-board 24.

In yet another preferred embodiment, a module having an internal lattice placement structure is used to slide the antenna and on board PC-board 24 into the IMD 30 and the telemetry port 10. It is appreciated that many different types and sizes of antenna 20 may be used without departing from the spirit and scope of the invention. It is further understood that there are many possible sizes and configurations for the telemetry port 10 without departing from the spirit and scope of the invention.

Referring now in particular to FIG. 1 there is shown an exploded view of the telemetry port 10 of the present invention in conjunction with an IMD 30. The telemetry port includes the housing 12 defining the void space 16 within the telemetry port 10. In this embodiment, the shell 32 of the IMD 30 includes segments 38 and 38'. The antenna 20 enters the shell 32 through segment 38 and projects upwards through the aperture 36 at the rim 34 of the shell 32 of the IMD 30, beyond the shell 32 of the IMD 30 and into the void space 16 of the telemetry port 10. There is shown the periphery 40 of the telemetry port 10. The periphery 40 mates with the IMD 30 at the aperture 36 of the rim 34 and forms a sealing engagement therewith.

Figure 2:
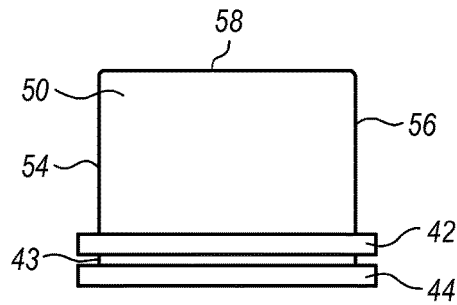
FIG. 2 is a side view of the telemetry port of the present invention.

FIG. 2 is a side view of a preferred embodiment of the telemetry port 10 of the present invention. As illustrated, the telemetry port 10 includes the top face 58 is positioned along a topmost edge of each of the first side wall 50, first lateral side 54 and second lateral side 56, the top face 58 extends from the first lateral side 54 to the second lateral side 56. The second lateral side 56 as shown is generally opposite to the first lateral side 54 and contiguous to the first side wall 50. FIG. 2 further illustrates the periphery 40 of the telemetry port 10 including the first band 42, the second band 44 and the ring 43, positioned therebetween and intermediate to the first band 42 and second band 44, the ring 43 further having a circumference that is generally smaller than the circumference of each of the first band 42 and the second band 44 such that the ring 43 forms a groove and is indented relative to each of the first band 42 and second band 44.

Figure 3:
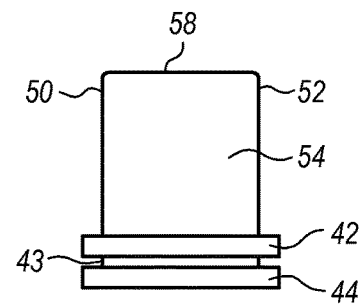
FIG. 3 is a front view of the telemetry port of the present invention.

FIG. 3 is a front view of the telemetry port of the present invention and further illustrates the embodiment shown in FIG. 2.

Figure 4:
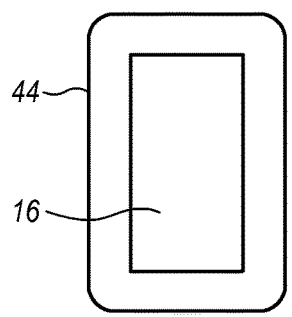
FIG. 4 is a bottom view of the telemetry port of the present invention.

FIG. 4 is a bottom view of the telemetry port of the present invention illustrating the bottom of the telemetry port 10. As shown, the second band 44 encompasses an opening for entry of the antenna 20 (not shown) into the void space 16.

Figure 5:
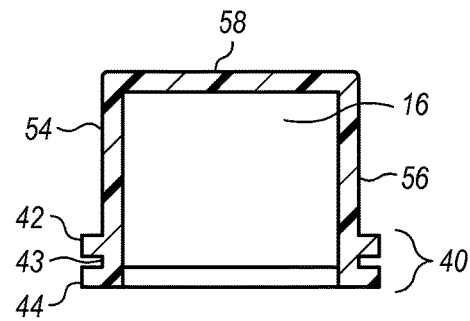
FIG. 5 is a cross sectional side view of the telemetry port of the present invention.

FIG. 5 is a cross sectional side view of the telemetry port 10 of the present invention. The void space 16 within the telemetry port 10 receives the antenna 20 (not shown) and allows the antenna 20 to transmit and receive telemetry signals without interference from the IMD 30 (not shown).

Figure 6:
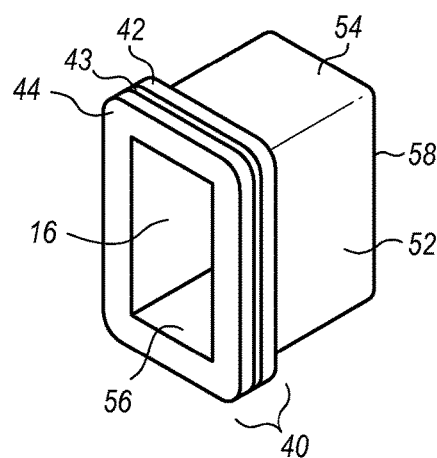
FIG. 6 is a side perspective view of the bottom of the telemetry port of the present invention.

FIG. 6 is a side perspective view of the bottom of the telemetry port 10 of the present invention. There is shown the second side wall 52, the first lateral side 54, the top face 58 is positioned along a topmost edge of each of the second side wall 52 and the first lateral side 54, the top face 58 is intermediate to the second side wall 52 and further extends therebetween, from the first side wall 50 (not shown) to the second side wall 52, and from the first lateral side 54 to the second lateral side 56 (not shown).

FIG. 7 is a side view of an alternative embodiment of the present invention and illustrates the shell 32 of the IMD 30 having two segments 38 and 38'.

FIG. 8 is a front view of an alternative embodiment of the present invention shown in FIG. 7 and illustrates the telemetry port 10 in conjunction with the IMD 30. The periphery 40 of the telemetry port 30 is in sealed mating engagement with the IMD 30 and connects to the IMD 30 at the aperture 36 of the rim 34 of the IMD 30. The antenna 20 is shown projecting within the void space 16 of the telemetry port 10.

FIG. 9 is a close-up view of the telemetry port 10 of the present invention as shown in FIG. 8. The gap 22 defined between the antenna 20 and the housing 12 is shown. The gap 22 is of sufficient size relative to the antenna 20, to allow for freedom of movement of the antenna 20 within the housing 12. The housing 12 of the telemetry antenna 10 includes the first side wall 50, the second side wall 52, the second side wall 52 being generally opposite to the first side wall 50, and the top face 58. The periphery 40 is in sealed mating engagement with the rim 34 of the IMD 30. As shown, when the periphery 40 of the telemetry port 10 and the rim 34 of the IMD 30 are in sealing engagement, the ring 43 is generally level with the rim 34 of the IMD 30, while the second band 44 mates with the IMD 30 below the rim 34 and the first band 42 mates with the IMD 30 above the rim 34.

In a preferred embodiment the dimensions of the telemetry port 10 are such that the first side wall 50, second side wall 52, first lateral side 54 and second lateral side 56 each have a thickness of generally 0.040 inches. In a preferred embodiment, the length measured from the top face 58 to the upper side of the second band 44 is generally 0.395 inches. In a preferred embodiment, the first lateral face 54 and second lateral face 56 each have a width of generally 0.310 inches. In a preferred embodiment, the side wall 50 and second side wall 52 each have a width of generally 0.520 inches. In a preferred embodiment, the ring 43 includes a thickness of generally 0.020 inches. In a preferred embodiment, the second band 44, has a thickness of generally 0.040 inches. The second band 44 extends below the rim 34 and beyond the aperture 36 generally by 0.040

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which the invention pertains and which fall within the limits of the appended claims.

What is claimed is:

1. A telemetry port for providing an open space in which an antenna may transmit and receive signals free from interference, the telemetry port comprising:
   a housing defining a void space therein for receiving an antenna within the void space, the void space further configured to provide the antenna positioned therein with sufficient space such that the antenna does not contact the housing,
   a gap defined within the void space, the gap being positioned between the antenna and the housing to allow for freedom of movement of the antenna within the housing, such that the antenna can move freely within the housing as a result of movement of the antenna without contacting the housing;
   the housing further defining a periphery positioned along a bottom edge of the housing, whereby the periphery is integrated to an implantable medical device, and forms a hermetic seal therewith;
   and wherein the periphery of the housing is configured to mate with the implantable medical device, the housing having a groove with a top surface and a bottom surface, wherein the bottom surface rests within an aperture positioned along a rim of a shell of the implantable medical device, wherein the groove receives a rim of the shell of the implantable medical device; and the top surface rests above the rim of the shell, and whereby the aperture of the shell provides a point of ingress and egress to the antenna from within the shell of the implantable medical device and the telemetry port.

2. The telemetry port of claim 1, wherein the periphery further comprises a first band, a second band and a ring, the ring being positioned intermediate to the first band and second band, the ring further having a circumference that is generally smaller than the circumference of each of the first band and the second band, such that the ring forms the groove and is indented relative to each of the first band and second band.

3. The telemetry port of claim 2, wherein the periphery is configured to mate with a rim of an implantable medical device.

4. The telemetry port of claim 3, wherein the ring is generally level with the rim of the implantable medical device, when the periphery of the telemetry port is in integrally mated with the implantable medical device.

5. The telemetry port of claim 4, wherein the first band is configured to mate with the implantable medical device, above the rim and the second band is configured to mate with the implantable medical device below the rim, when the periphery of the port is in sealed mating engagement with the implantable medical device.

6. The telemetry port of claim 1, wherein the housing comprises a first side wall and a second side wall, the second side wall being generally opposite to the first side wall, a first lateral side and a second lateral side, the second lateral side being generally opposite to the first lateral side and contiguous to the first side wall and second side wall, a top face positioned along a topmost edge of each of the first side wall, second side wall, first lateral side and second lateral side, the top face positioned intermediate to the first side wall and second side wall and further extending therebetween, from the first side wall to the second side wall, and from the first lateral side to the second lateral side.

7. The telemetry port of claim 1, wherein the material of the housing comprises a flexible clear plastic.

8. The telemetry port of claim 1, wherein the void space is configured to allow for ingress or egress of an antenna.

9. The telemetry port of claim 1, wherein the void space is configured to allow for ingress or egress of an antenna with an integrated PC board.

10. The telemetry port of claim 1, wherein only a portion of the antenna sufficient to receive and transmit telemetry signals projects within the void space.

11. The telemetry port of claim 1, wherein the void space is configured to allow for the free flow of telemetry signals.

12. The telemetry port of claim 1, wherein the housing comprises a material that is permeable to telemetry signals.

13. A method of manufacturing an implantable medical device comprising the steps of:
(a) providing a telemetry port, the telemetry port having an open space in which an antenna positioned therein may transmit and receive signals free from interference, the telemetry port comprising: a housing defining a void space therein for receiving an antenna within the void space, the void space further configured to provide the antenna positioned therein with sufficient space such that the antenna does not contact the housing, a gap defined within the void space, the gap being positioned between the antenna and the housing to allow for freedom of movement of the antenna within the housing, such that the antenna can move freely within the housing as a result of movement of the antenna without contacting the housing; the housing further defining a periphery positioned along a bottom edge of the housing, whereby the periphery is integrated to an implantable medical device, and forming a hermetic seal therewith; and wherein the periphery of the housing mates with the implantable medical device, the housing having a groove with a top surface and a bottom surface, wherein the bottom surface rests within an aperture positioned along a rim of a shell of the implantable medical device, wherein the groove receives the rim of the shell of the implantable medical device; and the top surface rests above the rim of the shell, and whereby the aperture of the shell provides a point of ingress and egress to the antenna from within the shell of the implantable medical device and the telemetry port;
(b) affixing the telemetry port to a portion of a shell of the implantable medical device;
(c) inserting the antenna within the shell of the implantable medical device;
(d) inserting at least a portion of the antenna within the telemetry port of the implantable medical device, whereby the portion of the antenna within the telemetry port is sufficient to transmit and receive signals; and
(e) hermetically sealing the telemetry port to the shell.

14. The method of claim 13, further comprising providing a module with an internal placement lattice structure whereby the antenna is slid into position within the shell and telemetry port.

15. The method of claim 13, wherein the telemetry port is hermetically sealed to the shell of the implantable medical device using laser or sonic welding.

\* \* \* \* \*